United States Patent [19]

Schneider et al.

[11] 4,178,168
[45] Dec. 11, 1979

[54] HERBICIDAL N-(HALOACETYL)-N-(N-METHYLENE PYRROLIDONYL)-2-OXYALKYLENEOXYALKYLANILINES

[75] Inventors: Louis Schneider, Elizabeth; David E. Graham, Westfield, both of N.J.

[73] Assignee: GAF Corporation, New York, N.Y.

[21] Appl. No.: 928,569

[22] Filed: Jul. 27, 1978

[51] Int. Cl.² .................. C07D 207/26; A01N 9/22
[52] U.S. Cl. .................... 71/95; 260/326.43;
    260/326.5 J; 260/575; 260/645
[58] Field of Search ............... 260/326.43; 71/95, 118

[56] References Cited
U.S. PATENT DOCUMENTS

| | | | |
|---|---|---|---|
| 3,769,301 | 10/1973 | Olin | 260/326.45 |
| 3,798,276 | 3/1971 | Bayer | 260/612 R |

Primary Examiner—Donald G. Daus
Assistant Examiner—Lisa Jones
Attorney, Agent, or Firm—Walter C. Kern; Walter Katz

[57] ABSTRACT

Herbicidal compounds having the formula:

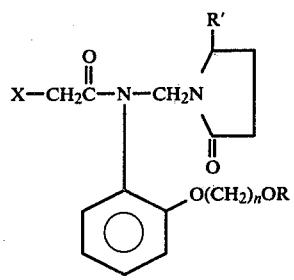

where
  n is 1–3,
  R is alkyl of 1–3 carbon atoms,
  R' is hydrogen or alkyl of 1–3 carbon atoms, and
  x is chloro or bromo,
are disclosed herein.

The compounds of the invention show good herbicidal activity, especially against wild grasses.

6 Claims, No Drawings

HERBICIDAL N-(HALOACETYL)-N-(N-METHYLENE PYRROLIDONYL)-2-OXYALKYLENEOXYALKYLANILINES

BACKGROUND OF THE INVENTION

1. Field of the Invention

This invention relates to novel N-(haloacetyl)-N-(N'-methylenepyrrolidonyl)-2-oxyalkyleneoxyalkylanilines which are useful herbicides.

2. Description of the Prior Art

U.S. Pat. Nos. 3,769,301 and 3,907,544 disclose related N-(acyl-tert-amidoalkyl)acetanilides, including N-methylenepyrrolidonyl derivatives; however, these compounds are substituted with 2,6-dialkyl groups only.

SUMMARY OF THE INVENTION

This invention describes herbicidal N-(haloacetyl)-N-(N'-methylenepyrrolidonyl)-2-oxyalkyleneoxyalkylanilines having the formula:

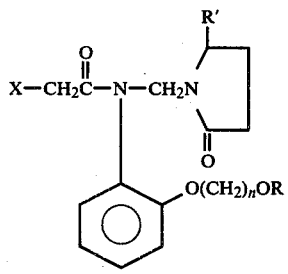

wherein
n is 1-3,
R is alkyl of 1-3 carbon atoms,
R' is hydrogen or alkyl of 1-3 carbon atoms, and,
X is chloro or bromo.

These compounds of the invention show good herbicidal activity, especially against wild grasses.

DETAILED DESCRIPTION OF THE PREFERRED EMBODIMENTS

The herbicidally active compounds of the present invention are obtained by a four-step process. In the first step, 2-nitrophenol is reacted with halogenated alkyl ethers in the presence of an acid acceptor to yield 2-oxyalkyleneoxyalkylnitrobenzenes. In the second step, the nitro group is reduced to the corresponding aniline. The third step of the process comprises reacting the aniline with a suitable N-methylolpyrrolidone to form the corresponding N-(N'-methylenepyrrolidonyl) intermediate. Finally, in step four, the intermediate is suitably acylated with a haloacetyl halide to form the desired compounds.

The reaction sequence is as follows:

Step 1:

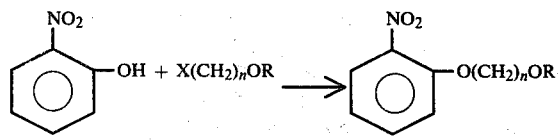

where
n is 1-3,
R' is 1-3, and
X is a halogen.

Step 2:

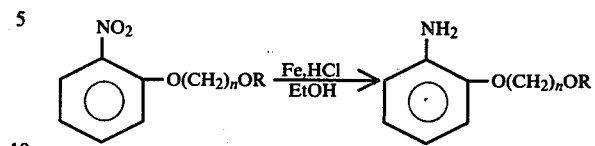

Step 3:

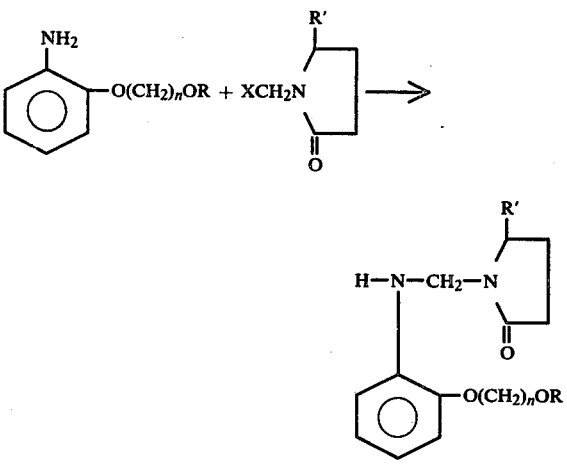

where
R' is hydrogen or alkyl of 1-3 carbon atoms, and
X is a halogen.

Step 4:

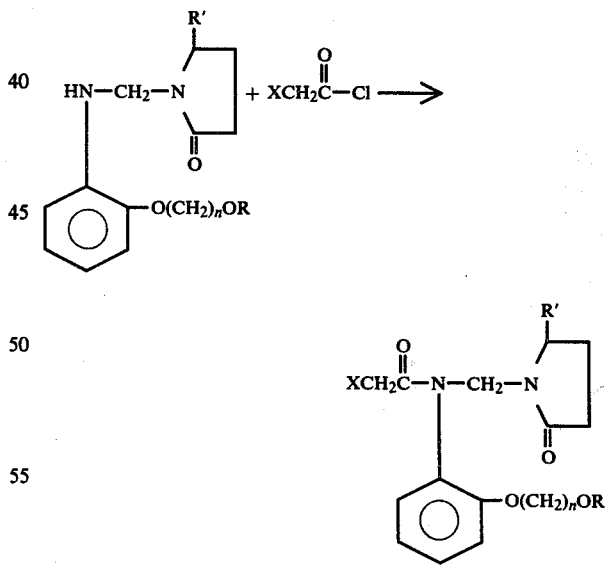

where
X is halogen.

As used herein, the term "alkyl" includes both straight and branched chained hydrocarbons. The term "halogen" includes chloro or bromo.

The compounds of this invention are especially useful as agricultural herbicides. They show particularly effective herbicidal activity against Japanese millet, foxtail millet and crabgrass.

Usually they are applied to the soil at the rate of about 1 to 25 lbs. per acre, or as a foliar spray on the weeds at concentrations of about 30 to 260 ppm., depending on various circumstances of the susceptibility of the weed to the herbicide, the weather, the stage of growth and various other factors. The material also may be applied as a dust. As a dust, it is practical to extend it with diluents, such as bentonite, chalk, clay, diatomaceous earth, fullers earth, mica, ground slate or any of the other usual carriers for agricultrual chemicals.

As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the weed.

Following are examples of preparation of the compounds of the invention and are presented by way of illustration and are not intended to be limiting unless otherwise specified.

EXAMPLE 1

N-Chloroacetyl-N-(N'-Methylenepyrrolidonyl)-2-Ethoxyethoxyaniline

A. 2-Ethoxyethoxynitrobenzene

2-Nitrophenol (91.0 g. 0.65 mole), 2-bromoethyl ethyl ether (100.0 g. 0.65 mole), anhydrous potassium carbonate (9.0 g, 0.72 mole) and acetone (1 liter) were refluxed for 65 hours. The reaction mixture was filtered, and the acetone removed by rotary evaporation. The residue was partitioned between 200 ml. of dichloromethane and 100 ml water. The organic phase was further washed with 200 ml. of 10% sodium hydroxide followed by 100 cc of water. The product (58.0 g) was obtained in 42% yield by a vacuum distillation (100°–120° C./0.5 mm).

B. 2-Ethoxyethoxyaniline

Iron 60 mesh (54.0 g, 0.96 mole), concentrated hydrochloric acid (15 cc), ethanol (260 cc) and water (230 cc) were heated to relux under a nitrogen blanket; 2-ethoxyethoxynitrobenzene (58.0 g, 0.28 mole) was added at reflux over 4 hours, and reflux continued for an additional 3 hours. The reaction mixture then was neutralized with concentrated ammonium hydroxide to a pH of 8–9, and filtered through a Celite bed. The iron cake was washed with 200 cc of ether, and the organic phase was separated. The product (20.0 g) was obtained in 40.2% yield by a vacuum distillation (111°–134° C./2–4 mm.)

C. N-Methylenepyrrolidonyl-2-ethoxyethoxyaniline

2-Ethoxyethoxyaniline (20.0 g, 0.11 mole), N-methylolpyrrolidone (13.5 g., 0.11 mole) and 100 cc xylene were refluxed under azeotropic conditions until the stoichiometric amount of water was removed (1.0 cc). The xylene layer then was washed with 2×50 cc of water, dried over magnesium sulfate and filtered. The xylene was removed by rotary evaporation. The crude product was solubilized in dichloromethane, and purified by column chromotography, using a 2.4:5.6:2.0 chloroform:hexane:acetone solvent system to yield 16.2 g of product; 53% yield.

D. To N-methylenepyrrolidonyl-2-ethoxyethoxyaniline (16.0 g, 0.056 mole), sodium carbonate (6.49, 0.060 mole) and toluene (50 cc) was charged chloroacetyl chloride (6.4 g, 0.060 mole) during ½ hour at 0°–5° C. The reaction mixture was allowed to warm up to 25° C. and maintained at 25° C. overnight. The toluene layer was washed with water, and separated. The solvent was removed by rotary evaporation, and the crude product crystallized from ether yielding 7.2 g. (36%); m.p. 64°–65° C.

EXAMPLE 2

N-Chloroacetyl-N-(N'-Methylenepyrrolidonyl)-2-Propoxymethoxyaniline

2-Nitrophenol, bromomethyl propyl ether, anhydrous potassium carbonate and acetone were reacted according to the procedure outlined in Example 1 to yield 2-propoxymethoxynitrobenzene, which was reduced to the corresponding aniline, and isolated by a vacuum distillation.

2-Propoxymethoxyaniline, N-methylolpyrrolidone and xylene then were condensed while removing water, and the intermediate reacted with chloroacetyl chloride in toluene in the presence of sodium carbonate, an acid acceptor, to form the desired product.

EXAMPLE 3

N-Chloroacetyl-N-(N'-Methylenepyrrolidonyl)-2-Methoxypropoxyaniline

2-Nitrophenol, 3-bromopropyl methyl ether, anhydrous potassium carbonate and acetone were reacted according to the procedure outlined in Example 1 to yield 2-methoxypropoxynitrobenzene, which was reduced to the corresponding aniline. The aniline was isolated by vacuum distillation.

2-Methoxypropoxyaniline, N-methylolpyrrolidone and xylene were condensed while removing water and further reacted with chloroacetyl chloride in toluene in the presence of sodium carbonate to form the desired product.

EXAMPLE 4

N-Chloroacetyl-N-(5-Methyl-N'-methylenepyrrolidonyl)-2-Ethoxyethoxyaniline

2-Ethoxyethoxyaniline, formed by alkylation and reduction of 2-nitrophenol, as described in Example 1, was condensed with 5-methyl-N-methylenepyrrolidone, and further reacted with chloroacetyl chloride to form the desired product.

EXAMPLE 5

Herbicidal Tests

Primary tests were made on two flats seeded with six species of representative monocotyledonous and dicotyledonous plants (Japanese millet, foxtail millet and crabgrass). The test chemical was applied to one such flat immediately after it was seeded. The other flat contained plants on which the first true leaves had developed. Both of these flats were sprayed, simultaneously, with the test chemical of 2080 ppm, a rate sufficient to give 10 lb/acre (104 mg in 50 ml of water on 144 square inches). Diuron, 3-(3,4-dichlorophenyl)-1,1-dimethylurea, as a standard, was applied pre-emergence at the rate of 2.5 lb/acre. The response was rated 12 to 21 days after treatment on a scale of 0 to 10 where 0 represents no injury and 10 represents complete kill.

Secondary tests were made at lower concentrations, namely, at 5 lbs/acre, against commercial Lasso, N- chloroacetyl-N-methoxymethyl-2,6-diethylaniline, as the standard.

TABLE 1

| | Pre-Emergence Herbicidal Ratings | | | |
| --- | --- | --- | --- | --- |
| | Primary (10 lbs/acre) | | Secondary (5 lbs/acre) | |
| Test Plant | Example 1 | Standard (Diuron) | Example 1 | Standard (Lasso) |
| Foxtail Millet | 8 | 10 | 8 | 10 |
| Japanese Millet | 10 | 10 | 10 | 10 |
| Crabgrass | 10 | 10 | 10 | 10 |

The tests demonstrate the effectiveness of the compounds of the invention against wild grasses.

While the invention has been described with particular reference to certain embodiments thereof, it will be understood that certain modifications and changes may be made which are within the skill of the art. Therefore it is intended to be bound only by the appended claims.

What we claim is:

1. Herbicidal N-(haloacetyl)-N-(N'-methylene-pyrrolidonyl)-2-oxyalkyleneoxyalkylaniline compounds having the formula:

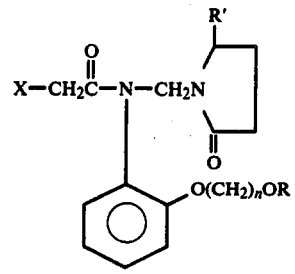

where
n is 1–3,
R is alkyl of 1–3 carbon atoms,
R' is hydrogen or alkyl of 1–3 carbon atoms, and,
X is chloro or bromo.

2. A compound according to claim 1 which is N-chloroacetyl-N-(N'-methylenepyrrolidonyl)-2-ethoxyethoxyaniline.

3. A compound according to claim 1 which is N-chloroacetyl-N-(N'-methylenepyrrolidonyl)-2-propoxymethoxyaniline.

4. A compound according to claim 1 which is N-chloroacetyl-N-(N'-methylenepyrrolidonyl)-2-methoxypropoxyaniline.

5. A compound according to claim 1 which is N-chloroacetyl-N-(N'-5-methyl-N'-methylenepyrrolidonyl)-2-ethoxyethoxyaniline.

6. A herbicidal composition of matter comprising:
a. a herbicidally effective amount of a compound of claim 1; and
b. an inert carrier.

* * * * *